(12) United States Patent
Takata et al.

(10) Patent No.: US 8,945,024 B2
(45) Date of Patent: Feb. 3, 2015

(54) MEDICAL WIRE

(75) Inventors: Hironori Takata, Setsu (JP); Jiro Ishida, Setsu (JP); Atsushi Ogawa, Kanagawa (JP)

(73) Assignees: Kaneka Medix Corporation, Osaka (JP); Kaneka Corporation, Osaka (JP)

( * ) Notice: Subject to any disclaimer, the term of this patent is extended or adjusted under 35 U.S.C. 154(b) by 573 days.

(21) Appl. No.: 11/576,799

(22) PCT Filed: Oct. 27, 2005

(86) PCT No.: PCT/JP2005/019802
§ 371 (c)(1),
(2), (4) Date: Apr. 5, 2007

(87) PCT Pub. No.: WO2006/046652
PCT Pub. Date: May 4, 2006

(65) Prior Publication Data
US 2007/0249924 A1    Oct. 25, 2007

(30) Foreign Application Priority Data
Oct. 29, 2004  (JP) .................. 2004-315130

(51) Int. Cl.
*A61B 5/00*    (2006.01)
*A61M 25/00*    (2006.01)
(Continued)

(52) U.S. Cl.
CPC . *A61B 17/12022* (2013.01); *A61B 2017/00292* (2013.01); *A61B 2017/00929* (2013.01);
(Continued)

(58) Field of Classification Search
USPC ............. 600/585; 606/1, 108, 195; 623/1.11; 604/531, 533–536, 538
See application file for complete search history.

(56) References Cited

U.S. PATENT DOCUMENTS 4,346,712 A * 8/1982 Handa et al. .................. 606/195
4,402,319 A * 9/1983 Handa et al. .................. 606/195
(Continued)

FOREIGN PATENT DOCUMENTS

JP    2641715    5/1997
JP    10-94542    4/1998
(Continued)

OTHER PUBLICATIONS

Extended European search report dated Nov. 20, 2012 issued in corresponding European application 05805316.6.

*Primary Examiner* — Adam Eiseman
(74) *Attorney, Agent, or Firm* — Birch, Stewart, Kolasch & Birch, LLP

(57) ABSTRACT

Disclosed herein is a medical wire with an intracorporeally indwelling member connected to the leading end part of a conductive wire through a thermally-fusible connecting member, wherein the contact of the leading end part of the conductive wire with the intracorporeally indwelling member can be surely prevented even when the connecting member is deformed.

The medical wire comprises a conductive wire and an intracorporeally indwelling member connected to the leading end part of the conductive wire through a thermally-fusible connecting member, in which the connecting member is heated and fused by a high-frequency current supplied through the conductive wire, thereby releasing the intracorporeally indwelling member, wherein a non-conductive spacer for preventing the contact of the intracorporeally indwelling member with the conductive wire is provided between them.

8 Claims, 2 Drawing Sheets

(51) Int. Cl.
  *A61M 25/16* (2006.01)
  *A61M 25/18* (2006.01)
  *A61M 39/00* (2006.01)
  *A61M 39/10* (2006.01)
  *A61F 2/06* (2013.01)
  *A61B 17/12* (2006.01)
  *A61B 17/00* (2006.01)

(52) U.S. Cl.
  CPC . *A61B17/12145* (2013.01); *A61B 2017/12068* (2013.01); *A61B 2017/00477* (2013.01); *A61B 17/12113* (2013.01)
  USPC .......... 600/585; 604/533; 623/1.11; 623/1.12

(56) References Cited

U.S. PATENT DOCUMENTS

| | | | | |
|---|---|---|---|---|
| 5,108,407 A * | 4/1992 | Geremia et al. | | 606/108 |
| 5,312,415 A * | 5/1994 | Palermo | | 606/108 |
| 5,350,397 A * | 9/1994 | Palermo et al. | | 606/200 |
| 5,423,829 A * | 6/1995 | Pham et al. | | 606/108 |
| 5,540,680 A * | 7/1996 | Guglielmi et al. | | 606/32 |
| 5,743,905 A * | 4/1998 | Eder et al. | | 606/32 |
| 5,759,161 A * | 6/1998 | Ogawa et al. | | 600/585 |
| 5,846,210 A * | 12/1998 | Ogawa et al. | | 600/585 |
| 5,964,797 A * | 10/1999 | Ho | | 606/194 |
| 5,984,929 A * | 11/1999 | Bashiri et al. | | 606/108 |
| 6,159,206 A * | 12/2000 | Ogawa | | 606/32 |
| 6,468,266 B1 * | 10/2002 | Bashiri et al. | | 606/1 |
| 6,478,773 B1 | 11/2002 | Gandhi et al. | | |
| 6,620,152 B2 * | 9/2003 | Guglielmi | | 606/1 |
| 6,743,236 B2 * | 6/2004 | Barry et al. | | 606/108 |
| 6,743,251 B1 * | 6/2004 | Eder | | 623/1.11 |
| 6,905,503 B2 * | 6/2005 | Gifford et al. | | 606/108 |
| 6,966,892 B2 * | 11/2005 | Gandhi et al. | | 604/114 |
| 7,179,276 B2 * | 2/2007 | Barry et al. | | 606/200 |
| 7,255,707 B2 * | 8/2007 | Ramzipoor et al. | | 606/200 |
| 7,972,342 B2 * | 7/2011 | Gandhi et al. | | 606/108 |
| 8,021,371 B2 * | 9/2011 | Ishida et al. | | 606/108 |
| 2002/0099408 A1 | 7/2002 | Marks et al. | | |
| 2003/0069539 A1 * | 4/2003 | Gandhi et al. | | 604/113 |
| 2004/0220563 A1 * | 11/2004 | Eder | | 606/41 |
| 2008/0103523 A1 * | 5/2008 | Chiu et al. | | 606/200 |

FOREIGN PATENT DOCUMENTS

| | | |
|---|---|---|
| JP | 2000-107191 | 4/2000 |
| JP | 2001-513390 | 9/2001 |
| WO | 0072781 A2 | 12/2000 |
| WO | 0158366 A1 | 8/2001 |

* cited by examiner

MEDICAL WIRE

CROSS-REFERENCE TO THE RELATED APPLICATIONS

This application is a national phase of the international application No. PCT/JP2005/019802 filed Oct. 27, 2005, the entire contents of which are incorporated by reference. This application also claims benefit of priority under 35 U.S.C. §119 to Japanese Patent Application No. 2004-315130 filed Oct. 29, 2004, the entire contents of which are incorporated by reference.

TECHNICAL FIELD

The present invention relates to a medical wire used to leave an intracorporeally indwelling member at an intended site in a vital body.

BACKGROUND ART

As a method for treating aneurysm or the like, which causes little invasion, there is currently known vascular embolization in which an intracorporeally indwelling member composed of a metal, which does not exert an adverse influence on a vital body, such as platinum is left within aneurysm. In this method, a medical wire with the intracorporeally indwelling member connected to the leading end part of a delivery wire is inserted into a catheter arranged in the vital body, the wire is operated under observation by a radiography to guide the intracorporeally indwelling member to a desired position within the vital body, whereby the intracorporeally indwelling member is caused to reach the intended site, and the intracorporeally indwelling member is released in this state.

As a method for releasing the intracorporeally indwelling member, there are known mechanical means and electrical means. For example, as an electrically releasing means, there is a means of supplying an electric current between a conductive wire and a counter electrode connected to the vital body from the outside to decompose and fuse a connecting member (see, for example, Patent Art. 1 and Patent Art. 2).

Patent Art. 2 discloses a medical wire for vascular embolization in which an intracorporeally indwelling member is connected to the leading end part of a conductive wire through a thermally-fusible rod-like connecting member composed of polyvinyl alcohol. According to this medical wire, a high-frequency electric current is applied between the conductive wire and the counter electrode, whereby the leading end part of the conductive wire functions as an electrode for heating to thermally fuse the connecting member in a moment, and the intracorporeally indwelling member is separated from the conductive wire, so that the medical wire is said to have merits that the time required for a surgical operation can be shortened and burdens imposed on a patient and a surgeon can be lightened.

Patent Art, 1: Japanese Patent Registration No. 3007022; and
Patent Art. 2: Japanese Patent Registration No. 2880070.

However, the rod-like connecting member composed of polyvinyl alcohol changes its form in the course of a swelling treatment with water or the like, which is required to use the medical wire, in such a manner that it expands in its radial direction and contracts in its axial direction (lengthwise direction), and moreover water is absorbed in the interior thereof by swelling, whereby it becomes flexible compared with that in a dry state, and so it is easily curved or bent. As a result, the connecting member composed of polyvinyl alcohol is crushed or bent in the catheter upon delivery of the intracorporeally indwelling member by the operation of the conductive wire when a route to an affected part is complicated, and a delivery resistance is high, so that the intracorporeally indwelling member may come into contact with the electrode part of the leading end of the conductive wire in some cases.

When it is specifically described, FIG. 5 is a cross-sectional view illustrating, on an enlarged scale, a joint portion between a conductive wire and an intracorporeally indwelling member in an exemplary conventional medical wire. As shown in FIG. 5, a coiled electrode part 12 is formed at a leading end part of a conductive wire 10 in this medical wire, a base end portion 14A of a rod-like connecting member 14 composed of polyvinyl alcohol is inserted into the coil of this electrode part 12 and fixed with an adhesive 16, a leading end portion 14B of the connecting member 14 is inserted into a coil forming an intracorporeally indwelling member 18 and fixed with an adhesive 20 likewise, the leading end of the electrode part 12 of the conductive wire 10 and the base end of the intracorporeally indwelling member 18 are separated from each other with a slight space, and the connecting member 14 is in an exposed state at this space portion. Reference numeral 22 designates a fluorocarbon resin coating provided on other portion than the leading end part and base end part of the conductive wire 10 and forming an insulating surface.

When the medical wire of such construction is subjected to a swelling treatment for use by placing it in water, however, polyvinyl alcohol forming the connecting member 14 absorbs water and swells. As a result, a portion of the connecting member 14, which is not fixed by the adhesives 16 and 20, expands and swells out in its radial direction and contracts in its axial direction as illustrated in FIG. 6, so that the leading end of the electrode part 12 of the conductive wire 10 approaches the base end of the intracorporeally indwelling member 18, and both may become a contacted state in some cases. Reference character 14S indicates a swollen-out portion formed in the connecting member 14.

In the state that the electrode part 12 of the conductive wire 10 has come into contact with the intracorporeally indwelling member 18, a high-frequency current flows into the intracorporeally indwelling member 18 when the current is supplied to the conductive wire 10, so that a member acting as the electrode part becomes a state that its surface area has increased to create a state that an impedance of a circuit formed by a power source device, the conductive wire 10, a vital body and a counter electrode has greatly decreased, and so the electrode part 12 does not sufficiently generate heat. As a result, fusion of the connecting member 14 is not surely achieved. After all, a situation that the intracorporeally indwelling member 18 cannot be released is brought about. This is attributable to the fact that heat (Joule heat) generated in the electrode part 12 depends on the impedance of the circuit, and the quantity of heat generated decreases when the impedance is low.

DISCLOSURE OF THE INVENTION

The present invention has been made on the basis of the foregoing circumstances and has as its object the provision of a medical wire with an intracorporeally indwelling member connected to the leading end part of a conductive wire through a thermally-fusible connecting member, wherein the contact of the leading end part of the conductive wire with the intracorporeally indwelling member can be surely prevented even when the connecting member is deformed.

A medical wire according to the present invention comprises a conductive wire and an intracorporeally indwelling member connected to the leading end part of the conductive wire through a thermally-fusible connecting member, in which the connecting member is heated and fused by a high-frequency current supplied through the conductive wire, thereby releasing the intracorporeally indwelling member, wherein a non-conductive spacer for preventing the contact of the intracorporeally indwelling member with the conductive wire is provided between them.

The above-described medical wire may be so constructed that the spacer has a hollow structure and is provided in a state that the connecting member has been inserted into an internal hole of the spacer.

The connecting member may preferably be composed of a polyvinyl alcohol resin.

The spacer may preferably substantially not swell with water and be composed of a thermoplastic or thermosetting resin, an adhesive cured or a polyvinyl alcohol resin.

According to the medical wire of the present invention, the contact of the intracorporeally indwelling member with the leading end of the conductive wire is prevented by the spacer provided between the intracorporeally indwelling member and the conductive wire, so that electric leak into the intracorporeally indwelling member is prevented to surely keep the quantity of heat generated at the electrode part, and so the connecting member is fused with certainty, whereby separation of the intracorporeally indwelling member can be surely conducted.

DESCRIPTION OF CHARACTERS

Figure 1:
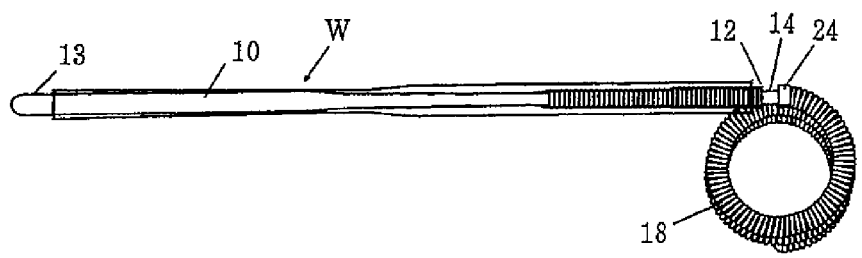
[FIG. 1] is a side elevation illustrating the construction of an exemplary medical wire according to the present invention.

W Medical wire
10 Conductive wire
12 Electrode part
13 Base end part
14 Connecting member
14A Base end portion
14B Leading end portion
14S Swollen-out portion
16, 20 Adhesives
18 Intracorporeally indwelling member
22 Fluorocarbon resin coating
24 Spacer
30 Catheter
B Vital body
32 High-frequency power source device
34 Counter electrode plate
Best Mode for Carrying Out the Invention An embodiment of the present invention will hereinafter be described in with reference to the drawings in the case where the medical wire is applied to coil embolization of aneurysm.

FIG. 1 is a side elevation illustrating the construction of an exemplary medical wire W according to the present invention. As illustrated in this drawing, this medical wire W is comprises a conductive wire 10, an intracorporeally indwelling member 18, a connecting member 14 for connecting the intracorporeally indwelling member 18 to the conductive wire 10, and a spacer 24.

Figure 2:
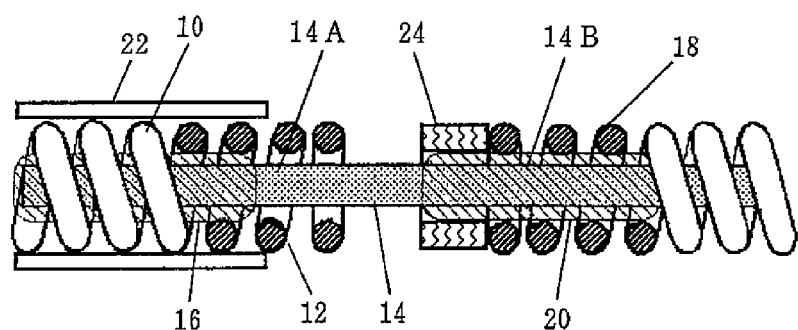
[FIG. 2] is a cross-sectional view illustrating, on an enlarged scale, a joint portion between a conductive wire and an intracorporeally indwelling member in the exemplary medical wire shown in FIG. 1.

When it is specifically described, a coiled electrode part 12 is formed at the leading end part of the conductive wire 10 as shown in FIG. 2, the base end portion 14A of the rod-like connecting member 14 composed of a thermally-fusible material is inserted into the coil of the leading end-side portion of the conductive wire 10, on which the electrode part 12 has been formed, and fixed with an adhesive 16, the leading end portion 14B of the connecting member 14 is inserted into a coil forming the intracorporeally indwelling member 18 and fixed with an adhesive 20, and the leading end of the electrode part 12 of the conductive wire 10 is separated from the base end of the intracorporeally indwelling member 18 with a space between them. In a state situated with such a space, the spacer 24 is provided and fixed to the connecting member 14. An insulating surface is formed with a fluorocarbon resin coating 22 on other portion than the leading end part and base end part 13 of the conductive wire 10.

Figure 3:
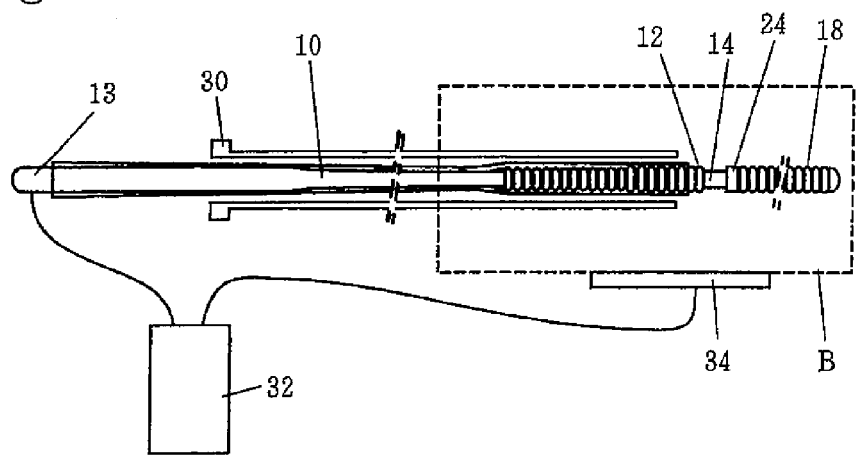
[FIG. 3] is an explanatory view illustrating a mode of using the medical wire shown in FIG. 1.

The conductive wire 10 serves to deliver the intracorporeally indwelling member 18 to the intended site through a catheter 30 (see FIG. 3). This conductive wire 10 is formed by covering the leading end part of a tapered wire body made of a stainless alloy, the diameter of which gradually decreases toward the leading end part thereof, with a stainless steel or platinum alloy coil fixed, and the coil of the leading end part forming the electrode part 12 preferably has, for example, an outer diameter of 0.25 mm or greater and an inner diameter of 0.12 mm or greater.

The intracorporeally indwelling member 18 is composed of a metal that does not adversely affect a vital body, and may have, as the form thereof, various forms, for example, a spiral form, an S-shaped form, a spiral form whose diameter varies, and a form to which a primary form and a secondary form are imparted. In particular, a secondary coil form, the primary form of which is a circular spiral form, and to which a circular secondary spiral form is imparted, is preferred.

As a material of a wire forming the intracorporeally indwelling member 18, may be used, for example, platinum, tungsten, gold, tantalum, iridium, and alloys composed of metals optionally selected from these metals, with platinum alloys or alloys composed of platinum and tungsten being particularly preferred. The sectional form of the wire is not limited to a circular form, and a form such as an elliptical form, square form or triangular form may be allowed. That obtained by processing a primary coil so as to have a secondary coil or three-dimensional form and roundly machining the leading end side thereof so as not to wound a vital body may also be preferably used.

The connecting member 14 is preferably composed of a thermally-fusible polyvinyl alcohol molding and thermally fused by heating by a high-frequency current supplied through the conductive wire 10. With respect to the dimensions thereof, for example, the outer diameter is at least 0.1 mm, the overall length is at least 1 mm, and lengths of portions inserted into the leading end part of the conductive wire 10 and the internal hole of the coil of the intracorporeally indwelling member 18 are preferably both at least 0.3 mm.

The spacer 24 has a ring-like form having a hollow structure having an internal hole over the overall length thereof and specifically has a cylindrical form. This spacer 24 is arranged between the electrode part 12 of the conductive wire 10 and the intracorporeally indwelling member 18 in a state that the connecting member 14 has been inserted into the internal hole thereof. In the illustrated embodiment, it is bonded and fixed to an external peripheral surface of the connecting member 14 with an adhesive at a position coming into contact with the intracorporeally indwelling member 18.

The inner diameter of the spacer 24 is a size fitted to the outer diameter of the connecting member 14, and the outer diameter thereof is preferably equal to or smaller than the outer diameters of the coil of the electrode part 12 of the conductive wire 10 and the coil of the intracorporeally indwelling member 18. For example, the outer diameter is at least 0.25 mm, the inner diameter is at least 0.12 mm, and the overall length is at least 0.1 mm.

No particular limitation is imposed on the material of the spacer 24 so far as it is non-conductive or has insulating property. However, it is preferably substantially not swollen with water. As specific examples thereof, may be mentioned those obtained by curing cyanoacrylate and epoxy adhesives, and the like. Those obtained by molding non-conductive materials including thermoplastic resins such as polyethylene, polypropylene and polyethylene terephthalate (PET), thermosetting resins such as polytetrafluoroethylene (PTFE), polyimide and silicone and resins such as polyvinyl alcohol may also be used.

The spacer 24 may be composed of a cured adhesive. Such a spacer 24 can be formed only by applying an adhesive to an external peripheral surface of the connecting member in a state projected outward and curing it and is advantageous in that the formation thereof is easy and the fact that the connecting member actually used has a considerably small diameter does not meet a great obstacle.

The medical wire W of the above-described constitution is used in the following manner. As illustrated in FIG. 3, the conductive wire 10 is inserted into a catheter 30 arranged in a vital body (patient) B to which the intracorporeally indwelling member 18 is applied and introduced into a blood vessel from a predetermined site within the vital body B to guide the intracorporeally indwelling member 18 to aneurysm while visually observing by fluoroscopy. This operation is carried out in a state that a gripping part extending to the base end part 13 on a side at hand (proximal side), on which the insulating surface of the conductive wire 10 is formed, has been grasped. Then, the electrode part 12 of the conductive wire 10, and portions located on the distal side from that, i.e., the electrode part. 12, the connecting member 14 and the intracorporeally indwelling member 18 are projected out of the leading end of the catheter 30, thereby creating a state that the intracorporeally indwelling member 18 has been inserted into the aneurysm.

On the other hand, a high-frequency power source device 32 is connected to between the base end part 13 of the conductive wire 10 and a counter electrode plate 34 provided in contact with the body surface of the vital body B, thereby forming an electrical circuit between the conductive wire 10 and the counter electrode plate 34. In the state that the intracorporeally indwelling member 18 has been inserted into the aneurysm, a high-frequency current for heating is supplied to the conductive wire 10 from the high-frequency power source device 32, whereby the electrode part 12 of the conductive wire 10 generates heat to heat the connecting member 14, and the connecting member 14 is fused to separate the intracorporeally indwelling member 18.

Figure 4:
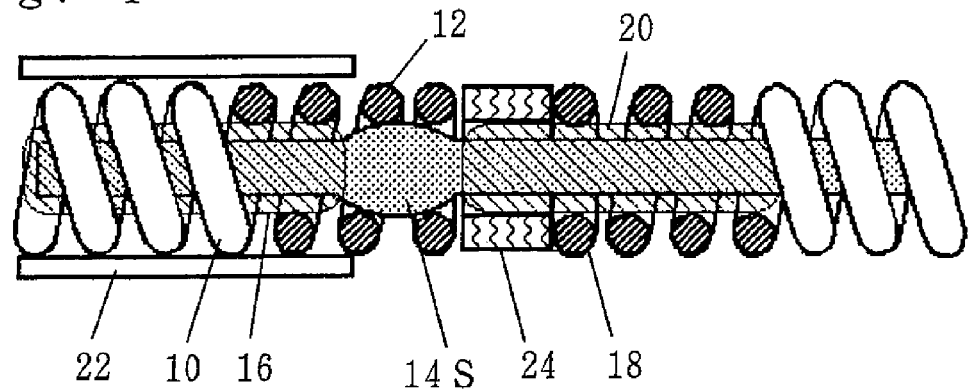
[FIG. 4] is a cross-sectional view illustrating a state that a connecting member has been swollen in the same joint portion as in FIG. 2.
Figure 5:
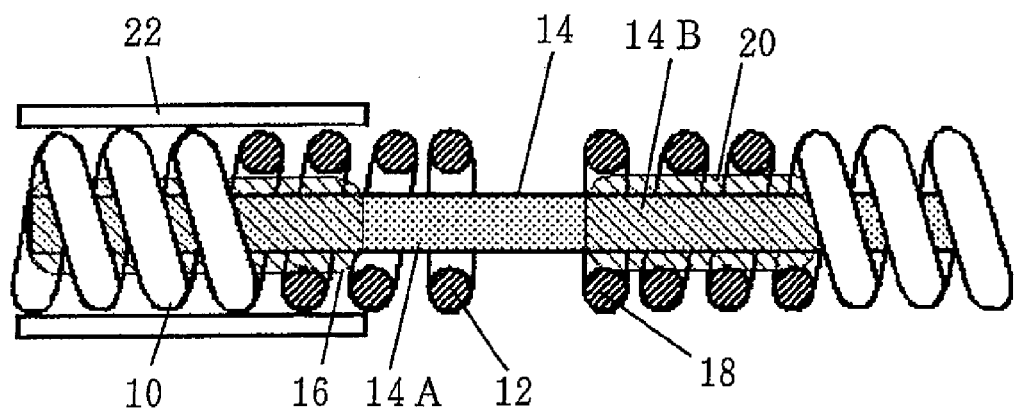
[FIG. 5] is a cross-sectional view illustrating, on an enlarged scale, a joint portion between a conductive wire and an intracorporeally indwelling member in an exemplary conventional medical wire.
Figure 6:
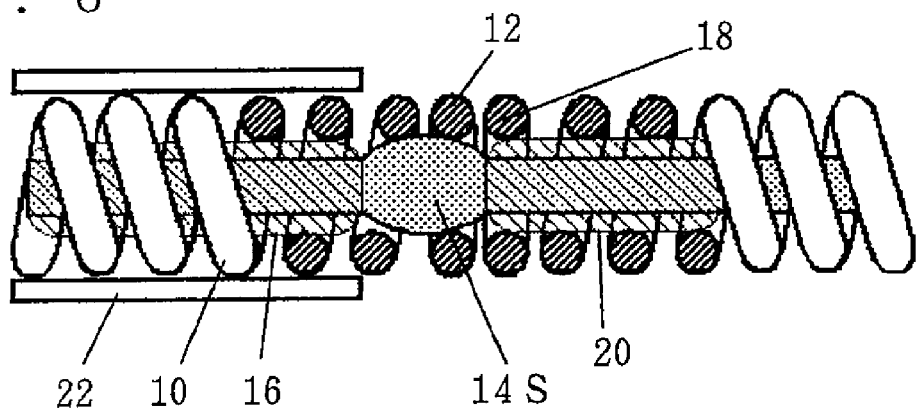
[FIG. 6] is a cross-sectional view illustrating a state that a connecting member has been swollen in the same joint portion as in FIG. 5.

In the above-described operation, it is necessary to swell a molded member of polyvinyl alcohol, which forms the connecting member 14, with water or the like in advance. When such a swelling treatment is conducted, the rod-like connecting member 14 causes a phenomenon that it expands and swells out in its radial direction to form a swollen-out portion 14S and contracts in its axial direction as illustrated in FIG. 4. In addition, water is absorbed in the interior thereof, whereby the flexibility of the connecting member 14 becomes high to be easily curved.

According to the medical wire W of the above-described constitution, the spacer 24 intervenes between the leading end part of the conductive wire 10 and the intracorporeally indwelling member 18, whereby the contact of the electrode part 12 of the conductive wire 10 with the intracorporeally indwelling member 18 can be surely prevented by the spacer 24 so as to be understood from FIG. 4 even when a route to an affected part upon delivery of the intracorporeally indwelling member 18 by the conductive wire 10 is complicated, and so a delivery resistance is high, so that the connecting member 14 is deformed within the catheter 30. As a result, leak of the current in the intracorporeally indwelling member 18 from the electrode part 12 is prevented.

As a result, expected heat is surely generated in the electrode part 12 of the conductive wire 10 by virtue of the high-frequency current supplied, and so the connecting member 14 can be heated and fused, whereby the intracorporeally indwelling member 18 can be released with certainty.

In the above, no particular limitation is imposed on the material and structure of the spacer and the mode of fitting to the conductive wire so far as it is non-conductive, by which the contact between the conductive wire and the intracorporeally indwelling member can be prevented.

For example, it is not essential that the form of the spacer is a hollow cylindrical form, and it is also not essential that it is fixed to the connecting member with the adhesive Accordingly, for example, a block-like spacer fixed to an external peripheral surface of the connecting member in a state projected outward, a ring-like spacer arranged in a state the connecting member has been inserted into it and provided in a state freely fitted to the connecting member without being fixed by the adhesive, or an interlocking type spacer of, for example, a ring-like or coiled form having a cut-out may be used. The spacer may also be fixed or held by the electrode part or the intracorporeally indwelling member. The number of spacers is also not limited, and a plurality of spacers may be used.

In the above-described embodiment, the case where the intracorporeally indwelling member is used in a treatment for the aneurysm has been described. However, the constitution of the present invention is not limited to medical wires used in specific treatments and can be applied to medical wires, in which the connecting member connecting the intracorporeally indwelling member to the electrode part of the conductive wire is fused by supplying a current to the conductive wirer whereby the intracorporeally indwelling member is separated.

The invention claimed is:

1. A medical wire comprising:
   a conductive wire having a coil form;
   a thermally-fusible connecting rod comprising a thermally fusible material;
   an intracorporeally indwelling member having a coil form comprising a metal; and
   a non-conductive spacer,
   wherein an end of the connecting rod is disposed in a leading end part of the coil of the conductive wire and another end of the connecting rod is disposed in the coil forming the intracorporeally indwelling member, so that the conductive wire and the intracorporeally indwelling member are connected by the connecting rod, wherein the connecting rod is heated and fused by a high-frequency current supplied through the conductive wire, thereby releasing the intracorporeally indwelling member, wherein the connecting rod is an insulator, wherein the non-conductive spacer is disposed between the intracorporeally indwelling member and the conductive wire, and the intracorporeally indwelling member, the spacer, and the conductive wire are aligned in an axial direction of the medical wire, in which the spacer prevents the electrical contact of the intracorporeally indwelling member with the conductive wire by being interposed therebetween, wherein the conductive wire is configured to deliver the intracorporeally indwelling member through a catheter, and wherein the spacer is disposed on the connecting rod so that the spacer is slidably movable on the connecting rod between the intracorporeally indwelling member and the conductive wire.

2. The medical wire according to claim 1, wherein the spacer has a hollow structure and is provided in a state that the connecting rod has been inserted into an internal hole of the spacer.

3. The medical wire according to claim 1 or 2, wherein the connecting rod is composed of a polyvinyl alcohol resin.

4. The medical wire according to any one of claim 1 or 2, wherein the spacer does not swell with water.

5. The medical wire according to any one: of claim 1 or 2, wherein the spacer is composed of a thermoplastic or thermosetting resin.

6. The medical wire according to any one of claim 1 or 2, wherein the spacer is composed of an adhesive cured.

7. The medical wire according to any one of claim 1 or 2, wherein the spacer is composed of a polyvinyl alcohol resin.

8. The medical wire according to claim 1 or 2, wherein the intracorporeally indwelling member is formed of a metal selected from the group consisting of platinum, tungsten, gold, tantalum, iridium, and alloys composed of metals selected from said group.

* * * * *